United States Patent [19]

Colescott et al.

[11] 4,105,602

[45] Aug. 8, 1978

[54] SYNTHESIS OF PEPTIDES WITH PARATHYROID HORMONE ACTIVITY

[75] Inventors: Robert L. Colescott, Bourbonnais, Ill.; Geoffrey W. Tregear, Hawthorne, Australia

[73] Assignee: Armour Pharmaceutical Company, Phoenix, Ariz.

[21] Appl. No.: 548,718

[22] Filed: Feb. 10, 1975

[51] Int. Cl.$^2$ .................... C08L 37/00; C07C 103/52
[52] U.S. Cl. .................... 260/8; 260/112.5 R
[58] Field of Search .................... 260/112.5 R, 8

[56] References Cited

U.S. PATENT DOCUMENTS

| | | | |
|---|---|---|---|
| 3,886,132 | 5/1975 | Brewer et al. | 260/112.5 R |
| 3,912,711 | 10/1975 | Leeman et al. | 260/112.5 R |
| 3,917,579 | 11/1975 | Bumpus et al. | 260/112.5 R |
| 3,987,014 | 10/1976 | Guiducci et al. | 260/112.5 R |
| 3,988,307 | 10/1976 | Gross | 260/112.5 R |
| 4,002,740 | 1/1977 | Goldstein et al. | 260/112.5 R |
| 4,022,760 | 5/1977 | Tinney | 260/112.5 R |

OTHER PUBLICATIONS

J. M. Stewart et al., "Solid Phase Peptide Synthesis", 1969, pp. 1–18.
Merrifield, Adv. in Enzymology, 32, 243–251 (1969).
Sakakibara et al.: Bull. Chem. Soc., Japan, 42, 1466 (1969).
Haslam, "Protective Groups in Organic Chemistry", J. McOmie, ed., Plenum Press, London, 1973, pp. 196–198.

*Primary Examiner*—Delbert R. Phillips
*Attorney, Agent, or Firm*—Richard R. Mybeck; Carl C. Batz

[57] ABSTRACT

Resin peptides useful in the preparation of peptides having biological activity, and particularly such resin peptides containing ®—CH$_2$—O—Phe—Asn at one end of an amino acid chain, ® being the resin and Phe and Asn being the residues of the amino acids phenylalanine and asparagine; and processes for the preparation of such resin peptides. Resin peptides are disclosed which contain amino acid chains identical with the amino acid chains of natural peptides having biological activity. Other resin peptides are disclosed which contain amino acid chains in which the amino acid residues differ in kind and sequence from amino acid chains of natural biologically active peptides but from which peptides having biological acitivity may be derived.

9 Claims, No Drawings

SYNTHESIS OF PEPTIDES WITH PARATHYROID HORMONE ACTIVITY

This invention relates to the synthesis of peptides and particularly resin peptides which are useful in the production of biologically active peptides. The invention involves such peptides as new compounds and also processes by which they may be produced.

BACKGROUND

It has long been known that certain natural biologically active substances can be obtained from the glands of animals and the substances so obtained utilized in the treatment of deficiencies of the human body. One such substance is the parathyroid hormone, commonly called PTH, which for many years has been obtained from the parathyroid glands of animals, particularly porcine and bovine parathyroid glands.

The burden of having to collect the relatively small parathyroid glands of animals at the time the animals are slaughtered, the limitation of the quantity of such glands which can be collected and the extensive purification procedures which are required to produce peptides which can be administered to humans, are indeed formidable disadvantages to the preparation of natural peptide hormones from animal glands. For many years the art has eagerly awaited the discovery of practical methods and compounds which enable the commercial synthesis of such peptides as human parathyroid hormone (HPTH). To our knowledge there have been no such compounds or methods prior to the discoveries of the present invention.

The human parathyroid hormone (HPTH) has been identified as having a sequence of 84 amino acids, its amino-terminal 1–34 sequence having the following structure:

Ser-Val-Ser-Glu-Ile-Gln-Leu-Met-His-Asn-Leu-Gly-Lys-His-Leu-Asn-Ser-
1   2   3   4   5   6   7   8   9   10  11  12  13  14  15  16  17

Met-Glu-Arg-Val-Glu-Trp-Leu-Arg-Lys-Lys-Leu-Gln-Asp-Val-His-Asn-Phe
18  19  20  21  22  23  24  25  26  27  28  29  30  31  32  33  34

Abbreviations Phe, Asn, His, etc. stand for the different amino acid groupings in the peptide chain and the numbers represents the positions of the amino acid groups in the chain according to accepted nomenclature. See the article by Niall et al, in Proc. Nat. Acad. Sci. U.S.A., 71, 384–388 (1974). This fragment appears to have full biological activity when compared to the full molecule.

It is a principal object of this invention to discover intermediate resin peptides from which biologically active peptides may be derived, particularly peptides with human parathyroid hormone activity, and to provide effective processes for the commercial production of such peptides. Other more specific objects will become apparent as this specification proceeds.

We are aware of disclosures of certain laboratory methods for the synthesis of certain peptides of relatively short amino acid chain lengths. These include an article by R. B. Merrifield entitled "Solid Phase Peptide Synthesis." I. "The Synthesis of a Tetrapeptide" at pages 2149 to 2154 in Vol. 85 of Journal of the American Chemical Society (1963) and a book entitled "Solid Phase Peptide Synthesis" by John W. Stewart and Janis D. Young published by W. H. Freeman and Company of San Francisco, Calif., but find in these publications no disclosures of resin peptides having amino groups of the kind and in the sequence involved in the present invention.

DESCRIPTION OF INVENTION

Our total synthesis involves many reactions by which many new intermediate resin peptides are formed and we will proceed with the description step by step, giving the structural formula, the general description and specific examples as we proceed.

In general, we utilize a solid phase synthesis whereby an insoluble polystryene resin, obtained by catalytic polymerization of styrene and divinyl benzene or as a core grafted with linear polystryene, is chloromethylated.

To the chloromethylated resin, we couple first phenylalanine, then asparagine and the other amino acids of the chain, in prescribed sequence, using a system of protection and deprotection of the active amine and carboxyl groups. Following the coupling of the last amino acid in the chain, the resin is cleaved from the peptide chain and the remaining protective groups removed. All amino acids are the naturally occurring L-isomers unless specifically defined.

Preparation of Insoluble Resin

An insoluble resin, hereinafter identified by the symbol ®, is a polymeric material which is insoluble in but solvated and penetrated by the the solvents used in peptide synthesis and is capable of providing an active receptor site for the first amino acid herein, namely, phenylalanine.

In practice, we find that we prefer to use either an insoluble polystyrene resin obtained by the catalytic polymerization of styrene and divinyl benzene, or by the grafting of linear polystyrene to a core of trifluorochloroethylene to form a (trifluorochloroethylene-g-(chloromethyl) styrene) polymeric resin. The resin, selected as indicated, is chloromethylated using chloromethylmethylether and stannic chloride catalyst according to the following reaction formula:

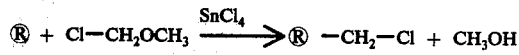

The chloromethylation reaction is specifically illustrated by the following examples 1 and 2.

EXAMPLE 1

One Kg of 2% divinylbenzene crosslinked polystyrene resin 200–400 mesh was washed with three 2 liter portions of methylene chloride. Fine particles were removed by draining the methylene chloride off the bottom each time. The resin was washed with two liters of the following solvents by suspension, stirring for ten minutes and filtration on a sintered glass Buchner: Two portions tetrahydrofuran, 2 portions water, 1 portion normal sodium hydroxide, 2 portions water, 2 portions dimethylformamide, 2 portions dioxane and 3 portions methanol. This washed resin was dried under vacuum at 60° C..

Five hundred grams of this washed polystyrene resin was stirred with 5 liters of chloromethyl methyl ether at room temperature and then the temperature was lowered to 0°–5° C. with an ice-water bath. Seventy-five grams of anhydrous stannic chloride in 925 ml ice-cold chloromethyl methyl ether was added and the mixture stirred in the ice-bath for 2 hours. The resin was filtered on a sintered glass Buchner and then washed with 2 liter portions of the following solvents: 25% water in dioxane, 25% two normal hydrochloric acid in dioxane, water and twice with methanol. The washed resin was dried under vacuum at 45°–50° C.. By this method the usual chloride content is between 0.7 to 1.0 milli-equivalent per gram.

EXAMPLE 2

For solid support a poly (trifluorochloroethylene-g-(chloromethyl) styrene) resin containing 11% polystyrene and chloromethylated to the extent of 0.13 M Mol/g Cl was also used instead of the divinylbenzene crosslinked polystryene resin.

Phenylalanine Esterification to the Polystyrene Resin

By our synthesis phenylalanine is first bonded to the polystyrene resin. This is described by the following formula:

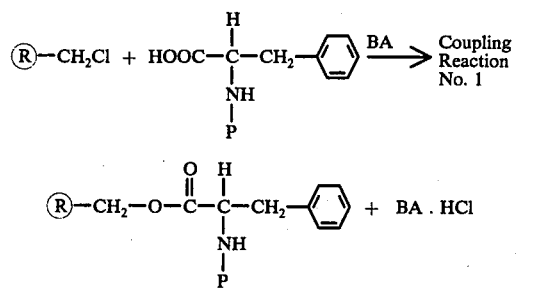

where Ⓡ is polystyrene resin, BA is a suitable base such as triethylamine, diisopropylamine, diisopropylethylamine, or alkali metal salt, and "P" is an amino protective group which preferably is tertiary-butyloxycarbonyl (BOC) but may be amyloxycarbonyl (AMOC) or ortho-nitrophenylsulfenyl (NPS).

As illustrated by the above formula the tert-butyloxycarbonyl-L-phenylalanine is attached to the chloromethylated resin in the presence of an acid acceptor. This reactor is demonstrated by the following specific Example 3.

EXAMPLE 3

Fifty grams of chloromethylated polystyrene resin, prepared as illustrated previously with a chlorine content of 0.74 milliequivalent (meq) per gram (37 meq chlorine) and 19.6 grams BOC-L-phenylalanine (74 meq) was stirred in 150 ml of absolute ethyl alcohol and then 9.77 ml of triethylamine (72 meq) was added and the mixture refluxed with stirring for 24 hours. The mixture was cooled, filtered on a sintered glass Buchner and washed on the Buchner with 500 ml portions of the following solvents: 2 times with 3A denatured alcohol, 2 times with dioxane, 2 times with 3A denatured alcohol, 2 times with water, 2 times with methanol. The resin was dried under vacuum at 40°–45° C.. Nitrogen analysis will show values varying from about 0.50 to 0.70 meq per gram. When the BOC protecting group was removed with trifluoroacetic acid as hereinafter described and the resin titrated to determine the available terminal amine group, this sample was found to approximate 0.38 meq per gram.

Deprotection and Neutralization

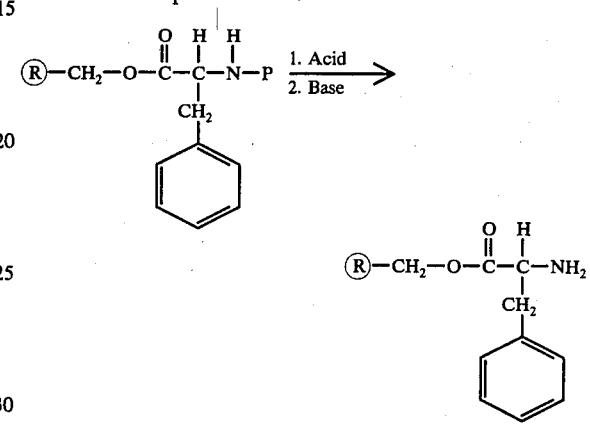

This resulting product is designated "Compound No. 1".

The deprotection of the amine function of the phenylalanine is accomplished by the removal of the protecting group using a suitable acid such as trifluoroacetic acid or hydrochloric acid. The resulting amine salt is then neutralized by treatment with a strong organic base. A specific example of this procedure is given in the following Example 4.

EXAMPLE 4

A 6 gram sample of the BOC-phenylalanine resin, as prepared by Example 3, was placed in the reaction vessel of a peptide synthesizer. The sample was washed twice with 40 ml portions of methylene chloride for two minutes each. Forty (40) ml of 50% trifluoroacetic acid in methylene chloride was added and the mixture reacted for 30 minutes. After filtration the resin was washed with three 40 ml portions of methylene chloride, 2 portions of methanol and 3 portions of chloroform, each wash being of 2 minute duration. Neutralization was accomplished by a 5 minute reaction with 40 ml of a 10% solution of diisopropylamine in chloroform. The resin was then washed 3 times with 40 ml of chloroform and 3 times with 40 ml of methylene chloride.

Coupling

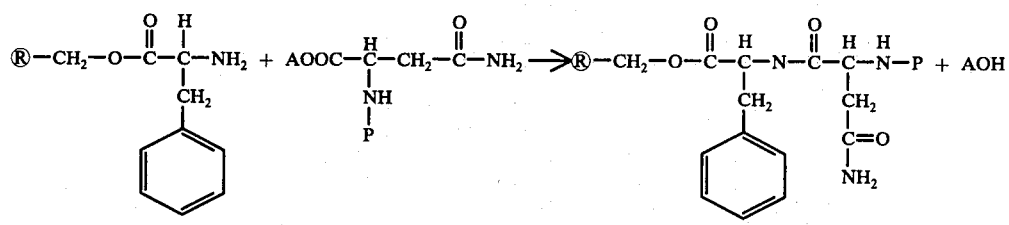

-continued
Coupling

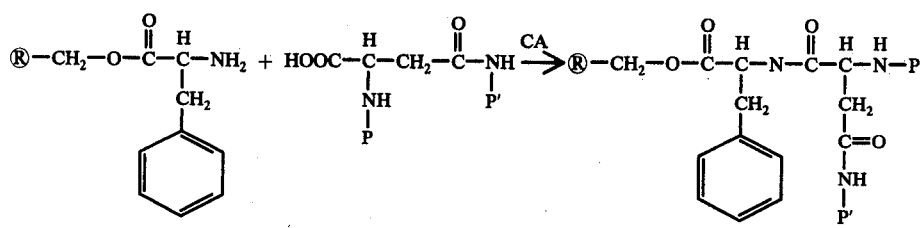

In this formula "P" is amino protective group, as described previously, "A" is an active ester such as p-nitrophenyl, o-nitrophenyl or penta-chlorophenyl, "P" can be hydrogen or an amide protective group such as benzhydryl, xanthydryl or the like and "CA" is a coupling agent which is preferably dicyclohexylcarbodiimide (DCC), but may be any coupling agent which forms peptide bonds, such as diimides, azides or mixed anhydrides. The symbols ®, P, P', and CA are to be taken as having the meanings above defined whenever they appear in the specification and claims.

Since the formula described previously begins to be cumbersome, we may rewrite the formula of the reaction product in the following manner:

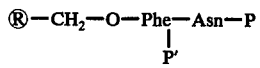

Wherein: "Phe" stands for phenylalanine residue, "Asn" stands for the asparagine residue and P' and P are as previously defined. This simplified nomenclature will be utilized in the description of all subsequent reactions.

Deprotection, as explained in connection with the phenylalanine resin results in a product bearing the following formula:

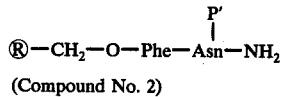

(Compound No. 2)

We believe that this resin peptide was made for the first time by our invention, and that this is an important link in the synthesis of the hormone, HPTH fragment.

Further we believe it is important that the coupling reaction be complete and have found the Ninhydrin test, described by E. Kaiser, R. Colescott, C. D. Bossinger and P. Cook in Anal. Biochem. 34, 595–98 (1970), to be applicable to determine when the coupling reaction is sufficiently complete. If the Ninhydrin test is negative we may proceed to the deprotection of the resin peptide and go on to the following coupling reaction. If this test is positive we repeat the coupling step until the Ninhydrin test result is finally negative.

Following are specific examples of the coupling of asparagine:

EXAMPLE 5

To a deprotected phenylalanine resin prepared according to Example 4 and having 3.5 meq of amine group was added a solution of 7 millimoles (approx. 100% excess) of BOC-L-beta-benzhydryl asparagine in 40 ml of methylene chloride. After two minutes a solution of 7 meq of dicyclohexylcarbodiimide (DCC) was added and the mixture agitated for 45 minutes. The product was filtered and washed twice each with 40 ml portions of chloroform and methylene chloride. The Ninhydrin test was performed on a 3–5 mg sample of resin peptide reaction product and found to be negative. This resin was then deprotected as was described in Example 4.

EXAMPLE 6

Two grams phenylalanine resin was deprotected and neutralized as described in Example 4. Three millimoles of NPS-L-beta-benzhydryl asparagine dissolved in 25 ml of methylene chloride, was added followed by three millimoles of dicyclohexylcarbodiimide. The mixture was agitated for one hour, filtered and washed with two portions of methylene chloride, two portions of methanol and three portions of methylene chloride.

EXAMPLE 7

In place of the NPS derivative in Example 6 we may substitute the AMOC derivative in the same meq amounts and the same results may be obtained.

EXAMPLE 8

Two grams of phenylalanine resin were deprotected and neutralized as described in Example 4, was washed three times with 25 ml of dimethylformamide and shaken for 20 hours with 6 meq of BOC-L-asparagine-P-nitrophenyl ester dissolved in 25 ml of dimethylformamide. The product was washed with two portions of dimethylformamide, two portions of methylene chloride, two portions of methanol and three portions of methylene chloride.

Synthesis of the Peptide

The following Table 1 lists in sequence the amino acids attached at each of reactions 2 to 34, indicating the position in the chain in which the attachment is made and listing the reactant used with the preferred protecting groups.

Table I

| Reaction No. | Position No. | Amino Acid Being Attached | Amino Acid Group With Preferred Protectants |
|---|---|---|---|
| 2 | 33 | asparagine | BOC-L-beta-benzhydryl-asparagine |
| 3 | 32 | histidine | BOC-L-im-carbobenzyloxy-L-histidine |
| 4 | 31 | valine | BOC-L-valine |
| 5 | 30 | aspartic acid | BOC-L-beta-benzylasparate |
| 6 | 29 | glutamine | BOC-L-glutamine-p-nitrophenyl ester |
| 7 | 28 | leucine | BOC-L-leucine |
| 8 | 27 | lysine | BOC-epsilon-2-chlorocarbobenzyloxy-L-lysine in 10% DMF for solubility |
| 9 | 26 | lysine | BOC-epsilon-2-chlorocarbobenzyloxy-L-lysine in |

Table I-continued

| Reaction No. | Position No. | Amino Acid Being Attached | Amino Acid Group With Preferred Protectants |
|---|---|---|---|
| 10 | 25 | arginine | BOC-L-tosylarginine in 20% DMF for solubility |
| 11 | 24 | leucine | BOC-L-leucine |
| 12 | 23 | tryptophane | BOC-L-tryptophane in 10% DMF for solubility |
| 13 | 22 | glutamic acid | BOC-L-gamma-benzylglutamate |
| 14 | 21 | valine | BOX-L-valine |
| 15 | 20 | arginine | BOC-L-tosylarginine in 20% DMF for solubility |
| 16 | 19 | glutamic acid | BOC-L-gamma-benzylglutamate |
| 17 | 18 | methionine | BOC-L-methionine |
| 18 | 17 | serine | BOC-O-benzyl-L-serine |
| 19 | 16 | asparagine | BOC-L-beta-benzhydryl-asparagine |
| 20 | 15 | leucine | BOC-L-leucine |
| 21 | 14 | histidine | BOC-im-carbobenzyloxy-L-histidine |
| 22 | 13 | lysine | BOC-epsilon-chlorocarbobenzyloxy-L-lysine in 10% DMF for solubility |
| 23 | 12 | glycine | BOC-glycine |
| 24 | 11 | leucine | BOC-L-leucine |
| 25 | 10 | asparagine | BOC-L-beta-benzyhydryl asparagine |
| 26 | 9 | histidine | BOC-im-carbobenzyloxy-1-histidine |
| 27 | 8 | methionine | BOC-L-methionine |
| 28 | 7 | leucine | BOC-L-leucine |
| 29 | 6 | glutamine | BOC-L-glutamine-p-nitrophenyl ester |
| 30 | 5 | isoleucine | BOC-L-isoleucine |
| 31 | 4 | glutamic acid | BOC-L-gamma-benzylglutamate |
| 32 | 3 | serine | BOC-O-benzyl-1-serine |
| 33 | 2 | valine | BOC-L-valine |
| 34 | 1 | serine | BOC-O-benzyl-1-serine |

As was described in connection with the attachment of asparagine in Reaction No. 2, (see Example 5), each succeeding reaction to attach another amino acid group involves the same procedure in which the resin peptide previously prepared is coupled with another protected amino acid derivative. The newly coupled is then deprotected and neutralized. More specifically, the following steps may in the case of each reaction be as follows:

Coupling 7 millimoles of the appropriate BOC-amino acid (0.43 equivalent excess in 40 ml of methylene chloride or DMF mixture where required).

7 millimoles of dicyclohexylcarbodiimide (coupling agent) in 15 ml of methylene chloride — 45 minutes reaction time.

2 × 40 ml chloroform washes — 2 minutes each.

2 × 40 ml — methylene chloride — 2 minutes each.

Deprotection

2 × 40 ml — chloride washes — 2 minutes each 40 ml 50% trifluoroacetic acid in methylene chloride — 5 minutes (After Reaction No. 12, 1% 2-mercaptoethanol or ethanedithiol is added to the 50% trifluoroacetic acid in methylene chloride.)

Deprotection, continued:

3 × 40 ml — methylene chloride washes — 2 minutes each.

2 × 40 ml — methanol washes — 2 minutes each.

3 × 40 ml — chloroform washes — 2 minutes each

Neutralization

2 × 40 ml — 10% diisopropylamine in chloroform — 5 minutes each

4 × 40 ml — chloroform washes — 2 minutes each

The procedures for making the coupling, the deprotection and neutralization steps in each of reactions 3 to 34 may be the same as already described in connection with reaction No. 2 except for the variations set forth in the following description.

As previously stated the Compound No. 2 which is the result of reaction No. 2 (after deprotection and neutralization) is:

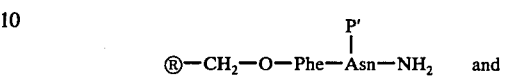 and

Compound No. 3, which is the result of reaction No. 3, is:

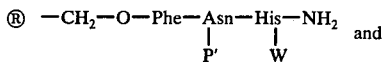 and

Compound No. 4, the result of reaction No. 4, is:

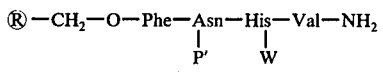

and, Compound No. 5, the result of reaction No. 5, is:

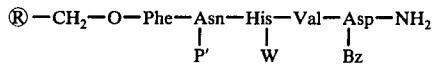

In reaction 3, at position 32, where histidine is attached, we prefer to use carbobenzyloxy (CBZ) protection for the imidazole, but may use tosyl or dinitrophenyl (DNP) protection. The symbol "W" is defined to mean CBZ, Tosyl or DNP. In Reaction 5, at Position 30, where aspartic acid is attached we prefer to use benzyl or benzyl derivative protection. The symbol "Bz" is defined to mean benzyl or benzyl derivative.

"Benzyl derivative" as used herein means those derivatives of the benzyl radical such as halogenated benzyl, alkylated benzyl or alkoxylated benzyl and the like. These derivates are well known to the peptide chemist and further characterization would be surplusage.

This pattern continues until the attachment of Gln at the 29th position. At this position the coupling agent DCC cannot be used unless the glutamine has a suitable protecting group, such as benzhydryl or xanthydryl, attached thereto. Without such protection, DCC creates a side reaction which destroys some of the glutamine. Alternatively, glutamine can be coupled, when unprotected, as an "active ester" as in Example 8.

The deprotected resin peptide is agitated with an active ester of glutamine such as p-nitrophenyl ester, o-nitrophenyl ester or pentachlorophenyl ester.

This coupling is demonstrated more specifically by the following Example 9.

EXAMPLE 9

The resin peptide represented by Compound No. 5 obtained as a result of reaction No. 5 (after deprotection and neutralization) was washed with three 40 ml portions of dimethylformamide for two minutes each. Twelve millimoles of BOC-L-glutamine-p-nitrophenyl ester dissolved in 40 ml of dimethylformamide was shaken with the resin for 20 hours, the resin was then washed with three portions of dimethylformamide, three portions of methanol and three portions of methylene chloride. The glutamine at Position 6, Reaction 29, is attached in this same manner.

EXAMPLE 10

If the amide group of the asparagine residues are unprotected, where P′ is hydrogen, then the asparagines at positions 33, 16 and 10 are attached in the manner of Example 8 using BOC-L-asparagine-p-nitrophenyl ester.

EXAMPLE 11

In place of the p-nitrophenyl ester of Examples 8, 9 and 10, either o-nitrophenyl ester or penta-chlorophenyl ester may be substituted, and the reaction carried out as set forth in Examples 8, 9 and 10 to accomplish the coupling of glutamine and asparagine.

The coupling at position 16 is followed by the usual deprotection and neutralization and this results in a resin peptide compound No. 19 and is represented by the following formula:

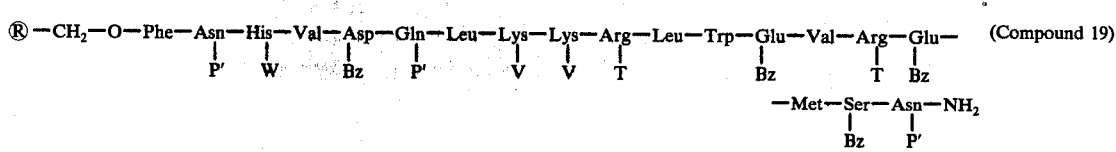
(Compound 19)

When lysine is attached, in Reaction No. 8, Position No. 27, we prefer to use as the epsilon amine protection agent 2-chlorocarbobenzyloxy (Cl-CBZ) but may also use carbobenzyloxy (CBZ), 2-bromocarbobenzyloxy, 2,4-dichlorocarbobenzyloxy or trifluoroacetyl (TFA).

We use the symbol "V" to indicate that the epsilon protection agent is one of those named groups.

For the coupling of the arginine amino acid in Reaction No. 10, at Position No. 25, we prefer to use as the guanidino protection agent the tosyl group (p-tolune sulfonyl), but may use a nitro group, and in the formula of this specification we employ the symbol "T" to mean tosyl or nitro.

The symbols T and V have the meanings as above throughout this specification and claims.

After each coupling reaction, and before deprotection of the resin peptide, we apply the Ninhydrin test. If the test is "positive" the coupling reaction last performed is repeated. If the test is "negative", we proceed to the deprotection of the resin peptide.

Upon the attachment of serine in Reaction 34, at the number one position, according to the manner and sequence above described, and after the deprotection and neutralization of the coupling resin peptide, we arrive at Compound No. 34 which has the following formula:

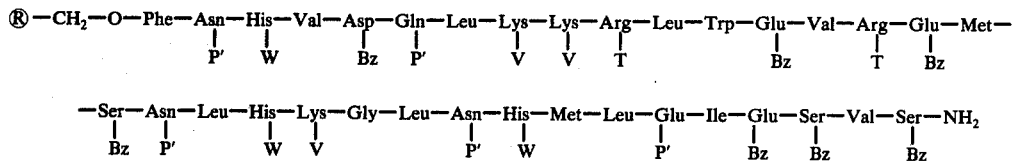

This resin peptide is then treated to remove the resin and the remaining protective groups. Suitably, the resin and most or all of the remaining protective groups may be removed by treatment with anhydrous hydrogen fluoride. The formula for this reaction is:

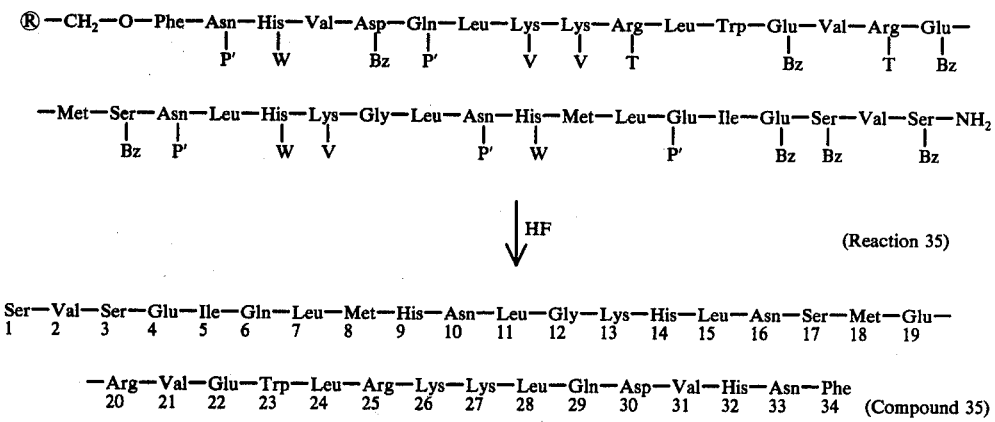

EXAMPLE 12

Two grams of compound 32 were placed in a Kel-F vessel with 2 mls of anisole and 10 mls of anhydrous hydrogen fluroide was added by distillation. This mixture was stirred at 0° C for 1 hour. The hydrogen fluoride was removed by vacuum distillation, the residue washed four times with ethyl acetate followed by extraction with glacial acetic acid. The acetic acid extract was lyophilized to give a fluffy white powder. This process removes the peptide from the resin and removes all protective groups on the amino acid.

Where V in Reaction 35 is TFA the reaction product is:

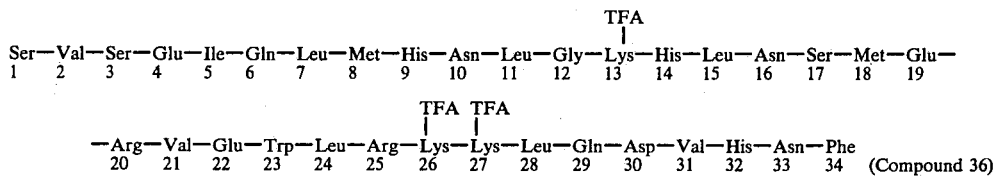

The following Example 13 illustrates the cleavage reaction when "V" is trifluoroacetyl (TFA).

EXAMPLE 13

Two grams of the blocked HPTH resin peptide were placed in a Kel-F vessel with 2 ml of anisole and 10 mls of anhydrous hydrogen fluoride was added by distillation. This mixture was stirred at 0° C for 1 hour. The hydrogen fluoride was removed by vacuum distillation, the residue washed 4 times with ethyl acetate followed by extraction with glacial acetic acid. The acetic acid extract was lyophilized to give 779 mg of a fluffy white powder. This process removes the peptide from the resin and removes all blocking groups on the difunctional amino acids except the trifluoroacetyl (TFA) blocking group of the lysine residues. Hence, this product is called TFA-HPTH peptide, (Compound 36).

EXAMPLE 14

In accordance with the invention, the polytrifluorochloroethylene-g-(chloromethyl)styrene) resin of Example 2 was esterified with BOC-L-phenylalanine and to the other 33 amino acids were attached thereto in the sequence specified to provide compound 35.

EXAMPLE 15

Using the coupling, deprotection and neutralization procedures described, a 1-34 resin peptide was prepared in which the No. 1 serine was replaced by alanine by reacting Compound 33 with BOC-L-alanine (instead of BOC-O-benzyl-L-serine). After removal of the resin and all of the remaining protecting groups, the formula of the reaction product is:

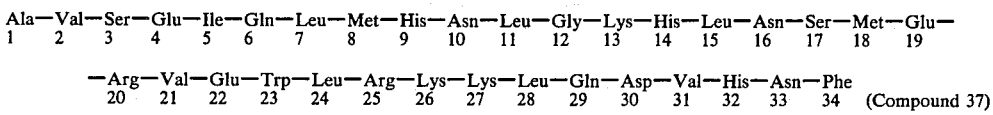

EXAMPLE 16

In the same manner as described in the previous examples, a 1-34 resin peptide was prepared in which the No. 1 L-serine was replaced by D-serine by treating Compound 33 with BOC-O-benzyl-D-serine (instead of BOC-O-benzyl-L-serine). After removal of the resin and all of the remaining protecting groups, the formula of the reaction product is:

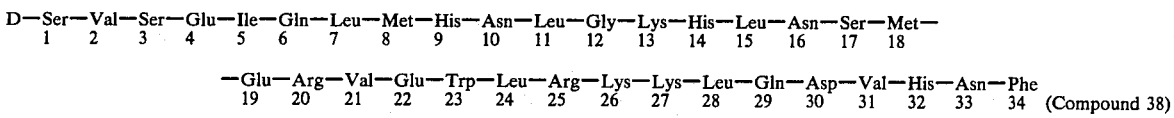

Purification

After gel filtrationn on Biogel P-6, (Biorad) the crude 1 to 34 human parathyroid hormone peptide [HPTH (1-34)] was chromatographed on carboxymethylcellulose (CMC) (Whatman CM52) using a linear gradient of ammonium acetate buffer. After desalting on polyacrylamide gel, the homogeneity of the synthetic peptides was checked by thin-layer chromatography on cellulose (Brinkmann Celplate-22, Eastman 6065) and silica gel (Merk) plates. The sample load was 30 ug in 5 ul of 0.1M acetic acid. The following solvent systems were used: $R_f{}^a$, n-butanol/acetic acid/water 4:1:5; $R_f{}^b$, ethyl acetate/pyridine/acetic acid/water 5:5:1:3; $R_f{}^c$, n-butanol/pyridine/acetic acid/water 15:10:3:12; $R_f{}^d$, n-butanol/acetic acid/water/ethyl acetate 1:1:1:1. The peptide spots were visualized by spraying the plates with Ehrlich reagent and 0.5% ninhydrin in ethanol. The purified synthetic HPTH (1-34) peptide gave a single spot with $R_f{}^a$ (cellulose, Brinkman) 0.19; $R_f{}^a$ (silica) 0.11; $R_f{}^b$ (silica) 0.17; $R_f{}^b$ (cellulose, Brinkman) 0.40; $R_f{}^c$ (cellulose, Eastman 6065) 0.66; and $R_f{}^d$ (cellulose, Brinkman) 0.48.

The biological activities of the snythetic HPTH (1-34) and the synthetic [Ala$^1$]HPTH (1-34) peptides in the in vitro Rat Kidney Adenylate Cyclase assay and the Chick Hypercalcemia Assay are shown in the following Table 2. Included for comparison are the corresponding data on the native bovine (1-84) [BPTH (1-84) (native)] and the synthetic bovine (1-34) [BPTH (1-34)] peptides, as well as the native Human PTH (1-84).

TABLE 2

| Biological Activity of Synthetic and Native Paraghyroid Hormones | |
|---|---|
| In vitro | In vivo |
| Rat Kidney Adenylate Cyclase [MRC u/mg] | Chick Hypercalcemin [MRC u/mg] |
| HPTH (1-84) (native) 350 | — |
| HPTH (1-34) 1030 | 7400 |
| BPTH (1-84) (native) 3000 | 2500 |
| BPTH (1-34) 5400 | 7700 |
| [Ala$^1$] HPTH (1-34) 4085 | 4600 |

From the foregoing it is apparent that methods and products have been herein described and illustrated which fulfill all of the foregoing objectives in a remarkable unexpected fashion. It is, of course, understood that the several examples herein presented are for explanatory and not limiting purposes, such modifications, alterations, and adaptions of this invention as may readily occur to the artisan when confronted with this disclo-

We claim:

1. A resin peptide having the structure:

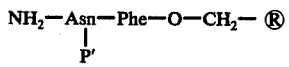

wherein:
Ⓡ is an insoluble polystyrene resin; and
P' is hydrogen, xanthydryl or benzhydryl.

2. A resin peptide having the structure;

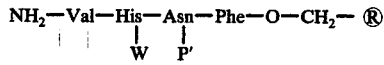

wherein:
Ⓡ is an insoluble polystyrene resin; and
P' is hydrogen, xanthydryl or benzhydryl
W is carbobenzyloxy, tosyl, or dinitrophenyl.

3. A resin peptide having the structure;

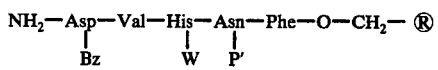

wherein:
Ⓡ is an insoluble polystyrene resin; and
P' is an hydrogen, xanthydryl or benzhydryl;
W is carbobenzyloxy, tosyl, or dinitrophenyl; and
Bz is benzyl, benzhydryl, halogenated benzyl, alkylated benzyl, or a alkoxylated benzyl.

4. A resin peptide having the structure:

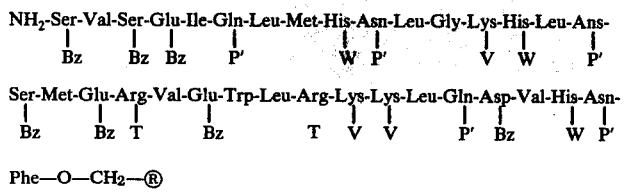

wherein:
Ⓡ is an insoluble polystyrene resin:
P' is hydrogen, xanthydryl, or benzhydryl;
T is tosyl or nitro;
V is 2-chlorocarbobenzyloxy, carbobenzyloxy, 2-bromocarbobenzyloxy, 2,4-dichlorocarbobenzyloxy, or trifluoroacetyl;
Bz is benzyl, benzhydryl, halogenated benzyl, alkylated benzyl alkoxylated benzyl; and
W is carbobenzyloxy, tosyl, or dinitrophenyl.

5. A peptide having the structure:

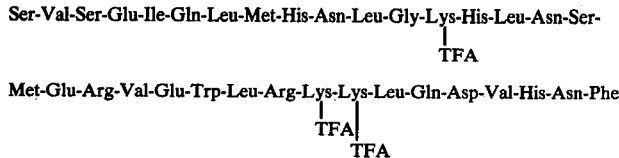

wherein: TFA is trifluoroacetyl.

6. A peptide having the structure: D-Ser-Val-Ser-Glu-Ile-Gln-Leu-Met-His-Asn-Leu-Gly-Lys-His-Leu-Asn-Ser-Met-Glu-Arg-Val-Glu-Trp-Leu-Arg-Lys-Lys-Leu-Gln-Asp-Val-His-Asn-Phe.

7. A resin peptide having the structure

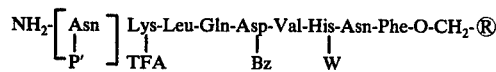

wherein:
Ⓡ is an insoluble polystyrene resin;
W is carbobenzyloxy, tosyl, or dinitrophenyl;
Bz is benzyl, p-methoxybenzyl, p-chlorobenzyl, p-nitrobenzyl or benzhydryl; and
TFA is trifluoroacetyl.

8. A resin peptide having the structure

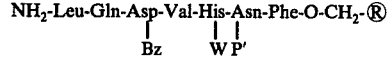

where
Ⓡ is an insoluble polystyrene resin:
P' is xanthydryl or benzhydryl;
Bz is benzyl, p-methoxybenzyl, p-chlorobenzyl, p-nitrobenzyl or benzhydryl; and
W is carbobenzyloxy, tosyl, or dinitrophenyl.

9. A resin peptide having the structure:

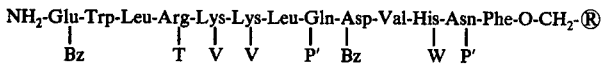

where
Ⓡ is an insoluble polystyrene resin;
P' is xanthydryl or benzhydryl;
Bz is benzyl, p-methoxybenzyl, p-chlorobenzyl, p-nitrobenzyl or benzhydryl;
W is carbobenzyloxy, tosyl, or dinitrophenyl;
T is tosyl or nitro; and
V is 2-chlorocarbobenzyloxy, 2-bromocarbobenzyloxy, or 2,4-dichlorocarbobenzyloxy.